US010857266B2

(12) United States Patent
Koob et al.

(10) Patent No.: US 10,857,266 B2
(45) Date of Patent: Dec. 8, 2020

(54) REINFORCED PLACENTAL TISSUE GRAFTS AND METHODS OF MAKING AND USING THE SAME

(71) Applicant: MiMedx Group, Inc., Marietta, GA (US)

(72) Inventors: Thomas J. Koob, Marietta, GA (US); Robert Tofe, Denver, CO (US); Elizabeth Chen, Denver, CO (US)

(73) Assignee: MiMedx Group, Inc., Marietta, GA (US)

(*) Notice: Subject to any disclaimer, the term of this patent is extended or adjusted under 35 U.S.C. 154(b) by 380 days.

(21) Appl. No.: 13/967,326

(22) Filed: Aug. 14, 2013

(65) Prior Publication Data

US 2014/0067058 A1    Mar. 6, 2014

Related U.S. Application Data

(60) Provisional application No. 61/808,171, filed on Apr. 3, 2013, provisional application No. 61/683,699, filed on Aug. 15, 2012.

(51) Int. Cl.
*A61L 27/14* (2006.01)
*A61F 2/02* (2006.01)
(Continued)

(52) U.S. Cl.
CPC .......... *A61L 27/54* (2013.01); *A61F 2/0063* (2013.01); *A61F 2/02* (2013.01); *A61L 27/14* (2013.01);
(Continued)

(58) Field of Classification Search
CPC ................. A61F 2/02; A61F 2/0063; A61F 13/00008–00017; A61L 27/24; A61L 27/3604; A61L 27/3633; A61L 27/14; A61L 27/44; A61L 27/54; A61L 27/56; A61L 2300/214; A61L 2300/20; A61L 2300/30; A61L 2300/412; A61L 2300/61; A61L 2430/00; A61L 2430/14; A61L 2430/34
(Continued)

(56) References Cited

U.S. PATENT DOCUMENTS 2,694,914 A    11/1954    Glover, Jr.
3,272,204 A *   9/1966    Artandi et al. ............... 606/151
(Continued)

FOREIGN PATENT DOCUMENTS

CN    101433556 A    5/2009
EP    0431164 A1    6/1991
(Continued)

OTHER PUBLICATIONS http://proxybiomedical.com/Images/ML005-01-Rev002.pdf (accessed on Jun. 5, 2014).*
(Continued)

*Primary Examiner* — Paul B Prebilic
(74) *Attorney, Agent, or Firm* — Alston & Bird, LLP

(57) ABSTRACT

Described herein are tissue grafts derived from the placental tissue that are reinforced with at least one biocompatible mesh. The tissue grafts possess good adhesion to biological tissues and are useful in wound healing applications. Also described herein are methods for making and using the tissue grafts.

13 Claims, 9 Drawing Sheets

(51) Int. Cl.
  *A61L 27/54* (2006.01)
  *A61L 27/44* (2006.01)
  *A61L 27/56* (2006.01)
  *A61L 27/36* (2006.01)
  *A61F 2/00* (2006.01)
  *A61L 27/24* (2006.01)
  *A61F 13/00* (2006.01)

(52) U.S. Cl.
  CPC .............. *A61L 27/24* (2013.01); *A61L 27/36* (2013.01); *A61L 27/3604* (2013.01); *A61L 27/44* (2013.01); *A61L 27/56* (2013.01); *A61F 13/00008* (2013.01); *A61L 27/3633* (2013.01)

(58) Field of Classification Search
  USPC ......... 623/23.71, 23.72, 23.73, 23.74, 23.75, 623/23.76
  See application file for complete search history.

(56) References Cited

U.S. PATENT DOCUMENTS

| | | |
|---|---|---|
| 4,564,368 A | 1/1986 | Sawyer et al. |
| 4,703,108 A | 10/1987 | Silver et al. |
| 4,745,771 A | 5/1988 | Linner et al. |
| 4,847,049 A | 7/1989 | Yamamoto |
| 4,968,325 A | 11/1990 | Black et al. |
| 5,118,867 A | 6/1992 | Bahrmann et al. |
| 5,284,655 A | 2/1994 | Bogdansky et al. |
| 5,541,232 A | 7/1996 | Howell et al. |
| 6,030,635 A | 2/2000 | Gertzman et al. |
| 6,387,369 B1 | 5/2002 | Pittenger et al. |
| 6,565,960 B2 | 5/2003 | Koob et al. |
| 6,936,271 B1 | 8/2005 | Oliver et al. |
| 7,101,857 B2 | 9/2006 | Sung et al. |
| 7,311,904 B2 | 12/2007 | Hariri |
| 7,311,905 B2 | 12/2007 | Hariri |
| 7,901,455 B2 | 3/2011 | Koob et al. |
| 8,067,044 B2 | 11/2011 | Henry et al. |
| 8,153,162 B2 | 4/2012 | Tseng et al. |
| 8,177,839 B2 | 5/2012 | Koob et al. |
| 8,192,481 B2 | 6/2012 | King |
| 8,231,908 B2 | 7/2012 | Kinoshita et al. |
| 8,323,701 B2 | 12/2012 | Daniel et al. |
| 8,357,403 B2 | 1/2013 | Daniel et al. |
| 8,372,439 B2 | 2/2013 | Daniel et al. |
| 8,623,421 B2 | 1/2014 | Daniel |
| 8,961,617 B2 | 2/2015 | Young |
| 10,350,049 B2 * | 7/2019 | Morse ................ A61L 27/3604 |
| 2002/0123141 A1 | 9/2002 | Hariri |
| 2002/0160510 A1 | 10/2002 | Hariri |
| 2003/0032179 A1 | 2/2003 | Hariri |
| 2003/0187515 A1 | 10/2003 | Hariri et al. |
| 2004/0028711 A1 | 2/2004 | Uchida et al. |
| 2004/0048796 A1 * | 3/2004 | Hariri et al. ............ 514/12 |
| 2005/0107876 A1 | 5/2005 | Kim et al. |
| 2006/0140913 A1 | 6/2006 | Bhatia |
| 2006/0166361 A1 | 7/2006 | Seyda et al. |
| 2006/0210532 A1 | 9/2006 | Carmeliet et al. |
| 2007/0020225 A1 | 1/2007 | Abramson et al. |
| 2007/0021762 A1 * | 1/2007 | Liu et al. ................ 606/157 |
| 2007/0071740 A1 | 3/2007 | Tseng et al. |
| 2007/0071828 A1 | 3/2007 | Tseng et al. |
| 2007/0202189 A1 | 8/2007 | Ahlfors |
| 2007/0248575 A1 | 10/2007 | Connor et al. |
| 2007/0299043 A1 | 12/2007 | Hunter et al. |
| 2008/0046095 A1 | 2/2008 | Daniel |
| 2008/0050347 A1 | 2/2008 | Ichim |
| 2008/0069895 A1 | 3/2008 | Liu et al. |
| 2008/0131966 A1 | 6/2008 | Hariri |
| 2008/0181967 A1 * | 7/2008 | Liu et al. ................ 424/583 |
| 2008/0233552 A1 | 9/2008 | Ma et al. |
| 2009/0012629 A1 | 1/2009 | Yao et al. |
| 2009/0036996 A1 * | 2/2009 | Roeber ................ 623/23.72 |
| 2009/0053290 A1 | 2/2009 | Sand et al. |
| 2009/0092664 A1 | 4/2009 | Mumper et al. |
| 2009/0142831 A1 | 6/2009 | Hariri |
| 2009/0175954 A1 | 7/2009 | Kinoshita et al. |
| 2009/0287308 A1 | 11/2009 | Davis et al. |
| 2009/0291891 A1 | 11/2009 | Neufeld |
| 2010/0028849 A1 | 2/2010 | Shelby et al. |
| 2010/0104539 A1 * | 4/2010 | Daniel et al. .............. 424/93.7 |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Stephen et al. |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0206776 A1 * | 8/2011 | Tom et al. ............... 424/583 |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2012/0135045 A1 | 5/2012 | Nixon et al. |
| 2012/0189571 A1 | 7/2012 | Sengupta et al. |
| 2012/0189583 A1 | 7/2012 | Liu et al. |
| 2012/0189586 A1 | 7/2012 | Harrell |
| 2012/0282348 A1 | 11/2012 | Yates et al. |
| 2012/0294910 A1 | 11/2012 | Daniel et al. |
| 2013/0230561 A1 | 9/2013 | Daniel et al. |
| 2013/0344162 A1 * | 12/2013 | Morse ................ A61K 35/12 424/582 |
| 2014/0052274 A1 * | 2/2014 | Koob ................ A61K 35/50 623/23.73 |
| 2014/0142025 A1 | 5/2014 | Koob |
| 2014/0142041 A1 | 5/2014 | Koob |
| 2014/0205646 A1 | 7/2014 | Morse et al. |
| 2014/0308233 A1 | 10/2014 | Koob |
| 2014/0356451 A1 | 12/2014 | Koob |

FOREIGN PATENT DOCUMENTS

| | | |
|---|---|---|
| EP | 0431479 A1 | 6/1991 |
| EP | 0 506 207 B1 | 9/1992 |
| EP | 0637452 | 2/1995 |
| KR | 10/1991/0011272 | 8/1991 |
| KR | 10/1991/0011727 | 8/1991 |
| KR | 2001100588 A | 11/2001 |
| WO | WO-87/00062 A1 | 1/1987 |
| WO | WO-88/03805 A1 | 6/1988 |
| WO | WO-01/08716 A1 | 2/2001 |
| WO | WO-2004/026244 | 4/2004 |
| WO | WO-2005/017165 | 2/2005 |
| WO | WO-2007/010305 | 1/2007 |
| WO | WO-2007/076522 | 7/2007 |
| WO | WO-2007/083984 A1 | 7/2007 |
| WO | WO-2009/033160 A1 | 3/2009 |
| WO | WO-2009/048908 | 4/2009 |
| WO | WO-2009/132186 A1 | 10/2009 |
| WO | WO-2010/029344 A2 | 3/2010 |
| WO | WO-2011/103470 | 8/2011 |
| WO | WO-2012/003377 | 1/2012 |
| WO | WO-2012/069559 A1 | 5/2012 |
| WO | WO-2012/112410 A2 | 8/2012 |
| WO | WO-2012/112417 A2 | 8/2012 |
| WO | WO-2012/112441 A1 | 8/2012 |
| WO | WO-2013/095830 A1 | 6/2013 |

OTHER PUBLICATIONS

MiMedx Press Release, "MiMedx Scientific Study is Electronically Published in the International Wound Journal", 2013.
PCT International Preliminary Report on Patentability dated Jan. 16, 2014 in PCT Patent Application No. PCT/US12/66862.
U.S. Appl. No. 13/647,308, filed Oct. 8, 2012, Daniel et al.
U.S. Appl. No. 13/688,091, filed Nov. 28, 2012, Spencer et al.
U.S. Appl. No. 13/719,148, filed Feb. 13, 2012, Morse et al.
U.S. Appl. No. 13/744,331, filed Jan. 17, 2013, Koob et al.
U.S. Appl. No. 13/744,332, filed Jan. 17, 2013, Pringle et al.

(56) References Cited

OTHER PUBLICATIONS

U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,753, filed Mar. 15, 2013, Koob et al.
U.S. Appl. No. 13/815,784, filed Mar. 15, 2013, Koob et al.
U.S. Appl. No. 13/815,873, filed Mar. 15, 2013, Brown et al.
U.S. Appl. No. 13/963,984, filed Aug. 9, 2013, Daniel et al.
U.S. Appl. No. 13/983,301, filed Feb. 13, 2012, Morse et al.
U.S. Appl. No. 14/050,218, filed Oct. 9, 2013, Brown et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Product Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Mayfield et al., "Watertight closure of spinal dura mater: Technical note," J. Neurosurg., (1975), 43(5):639-640.
PCT International Preliminary Report on Patentability for copending PCT Application No. PCT/US2012/024798, dated Feb. 1, 2013.
PCT International Search Report and Written Opinion for copending PCT Application No. PCT/US2013/054319, dated Nov. 13, 2013.
PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2013/054322, dated Oct. 22, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
PCT International Search Report for copending PCT Application No. PCT/US2012/024798, dated Jun. 20, 2012.
Tao, et al., "Implantation of amniotic membrane to reduce postlaminectomy epidurla adhesions," Eur. Spine. J., (2009), 18:1202-1212.
Koob et al., "Biological properties of dehydrated human amnion-chorion composite graft: implications for chronic wound healing", International Wound Healing, 2013, 10(5):493-500.
PCT International Search Report and Written Opinion dated Jan. 9, 2014 in related PCT Patent Application No. PCT/US2013/064146.
Nagaya et al., "Transplantation of mesenchymal stem cells improves cardiac function in a rat model of dilated cardiomyopathy", Circulation, 2005, 112(8):1128-1135.
Parolini et al., "Toward cell therapy using placenta-derived cells: disease mechanisms, cell biology, preclinical studies, and regulatory aspects at the round table", Stem Cells and Development, 2010, 19(2):143-154.
PCT International Search Report and Written Opinion for Patent Application No. PCT/US2013/063736, dated Aug. 12, 2014.
PCT International Search Report and Written Opinion for PCT Patent Application No. PCT/US2014/012141, dated May 20, 2014.
PCT International Preliminary Report of Patentability for PCT Patent Application No. PCT/US2013/0064146, dated Sep. 25, 2014.
Borkow et al., "Reducing the risk of skin pathologies in diabetics by using copper impregnated socks", Medical Hypotheses, 2009, 1-4, doi:10.1016/j.mehy.2009.02.050.
Database WPI XP002732611 & KR 2001-0100588, dated Nov. 14, 2001—Abstract.
Extended European Search Report dated Dec. 2, 2014, for European Patent Application No. EP 12746721.
PCT International Preliminary Report on Patentability dated Nov. 28, 2014, for International Patent Application No. PCT/US2013/054319.
PCT International Preliminary Report of Patentability for PCT Application No. PCT/US2013/054320 dated Feb. 26, 2015.
PCT International Preliminary Report on Patentability dated Nov. 27, 2014, for International Patent Application No. PCT/US2013/055003.
PCT International Preliminary Report on Patentability dated Dec. 8, 2014, for International Patent Application No. PCT/US2013/054322.
PCT International Preliminary Report on Patentability dated Feb. 14, 2013 for PCT Patent Application No. PCT/US2012/024814.
PCT International Search Report and Written Opinion for PCT Patent Application No. PCT/US2012/024814 dated Aug. 16, 2012.
PCT International Preliminary Report on Patentability dated Dec. 30, 2014, for International Patent Application No. PCT/US2013/063736.
PCT International Search Report and Written Opinion for PCT Appl. PCT/US2013/063736, dated Aug. 12, 2014.
PCT International Preliminary Report on Patentability dated Jan. 16, 2014 for PCT Patent Application No. PCT/US2012/066862.
PCT International Search Report and Written Opinion for PCT Application No. PCT/US2012/065672, dated Feb. 8, 2013.
PCT International Preliminary Report of Patentability for PCT Patent Application No. PCT/US2013/064146, dated Sep. 25, 2014.
PCT International Search Report and Written Opinion dated Apr. 13, 2015 for PCT Patent Application No. PCT/US15/12087.
PCT International Search Report and Written Opinion for PCT Application No. PCT/US2014/012141, dated May 20, 2014.
PCT International Preliminary Report on Patentability dated Nov. 10, 2014 in PCT Patent Application No. PCT/US2013/067623.
PCT International Search Report and Written Opinion dated Apr. 21, 2014 in related PCT Patent Application No. PCT/US2013/067623.
PCT International Preliminary Report on Patentability dated Dec. 30, 2014 in PCT Patent Application No. PCT/US2013067622.
PCT International Search Report and Written Opinion dated Apr. 16, 2014 in related PCT Patent Application No. PCT/US2013/067622.
PCT International Search Report and Written Opinion dated Apr. 22, 2014 in related PCT Patent Application No. PCT/US2013/67620.
PCT International Search Report and Written Opinion dated Aug. 26, 2014 in PCT Patent Application No. PCT/US2014/033346.
PCT International Preliminary Report of Patentability for PCT Application No. PCT/US2014/028975 dated Feb. 6, 2015.
PCT International Search Report and Written Opinion dated Jul. 24, 2014 for PCT Application No. PCT/US2014/028975.
PCT International Search Report and Written Opinion dated Dec. 30, 2014 in PCT Patent Application No. PTC/US2014/054603.
PCT International Search Report and Written Opinion dated Dec. 29, 2014 for PCT Patent Application PCT/US2014/053270.
PCT International Preliminary Report on Patentability dated Dec. 3, 2014 in PCT Patent Application No. PCT/US2013/067618.
PCT International Search Report and Written Opinion dated Apr. 22, 2014 in related PCT Patent Application No. PCT/US13/67618.
Toda A, et al., "The potential of amniotic membrane/amnion-derived cells for regeneration of various tissues." Journal of Pharmacological Sciences 2007, 105:215-228.
PCT International Search Report and Written Opinion for International Patent Application No. PCT/US2015/047303 dated Nov. 26, 2015. 13 pages.
Office Action for European Application No. 13830009.0 dated Mar. 26, 2019, 7 pages.

\* cited by examiner

REINFORCED PLACENTAL TISSUE GRAFTS AND METHODS OF MAKING AND USING THE SAME

CROSS REFERENCE TO RELATED APPLICATIONS

This application claims priority to U.S. Provisional Application Ser. No. 61/683,699, filed on Aug. 15, 2012 and U.S. Provisional Application Ser. No. 61/808,171 filed on Apr. 3, 2013, the entirety of both which are incorporated herein by reference.

BACKGROUND

Human placental membrane (e.g. amniotic membrane) has been used for various types of reconstructive surgical procedures since the early 1900s. However, the physical attributes of placental allografts do limit their use. For example, placental allografts cannot be sutured, limiting their utility with clinicians who feel suturing prevents micro movement which can disrupt the clot and subsequent blood supply to the grafted area, or prefer to first tack the barrier membrane in place and then add the bone graft. Placental allografts, traditional cadaveric allograft, and xenograft collagen barrier membranes are adaptable and conformable; however, they possess inadequate tensile strength and stiffness to stabilize grafted bone in alveolar horizontal and/or vertical bone augmentations.

SUMMARY

Described herein are tissue grafts derived from the placental tissue that are reinforced with at least one biocompatible mesh. The tissue grafts possess good adhesion to biological tissues and are useful in would healing applications. Also described herein are methods for making and using the tissue grafts.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 8-11 are sometimes referred to as FIGS. 90-93, respectively.

DETAILED DESCRIPTION

Before the present invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cross-linking agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism including mammals such as domesticated animals and primates such humans.

The term "amnion" as used herein includes amniotic membrane where the intermediate tissue layer is intact or has been substantially removed.

The term "placental tissue" refers to any and all of the well-known components of the placenta including but not limited to amnion, chorion, Wharton's Jelly, and the like. In one preferred embodiment, the placental tissue does not include any of the umbilical cord components (e.g., Wharton's jelly, umbilical cord vein and artery, and surrounding membrane).

Titles or subtitles may be used in the specification for the convenience of a reader, which are not intended to influence the scope of the present invention. Additionally, some terms used in this specification are more specifically defined below.

I. Reinforced Tissue Grafts and Methods for Making Thereof

Figure 1:
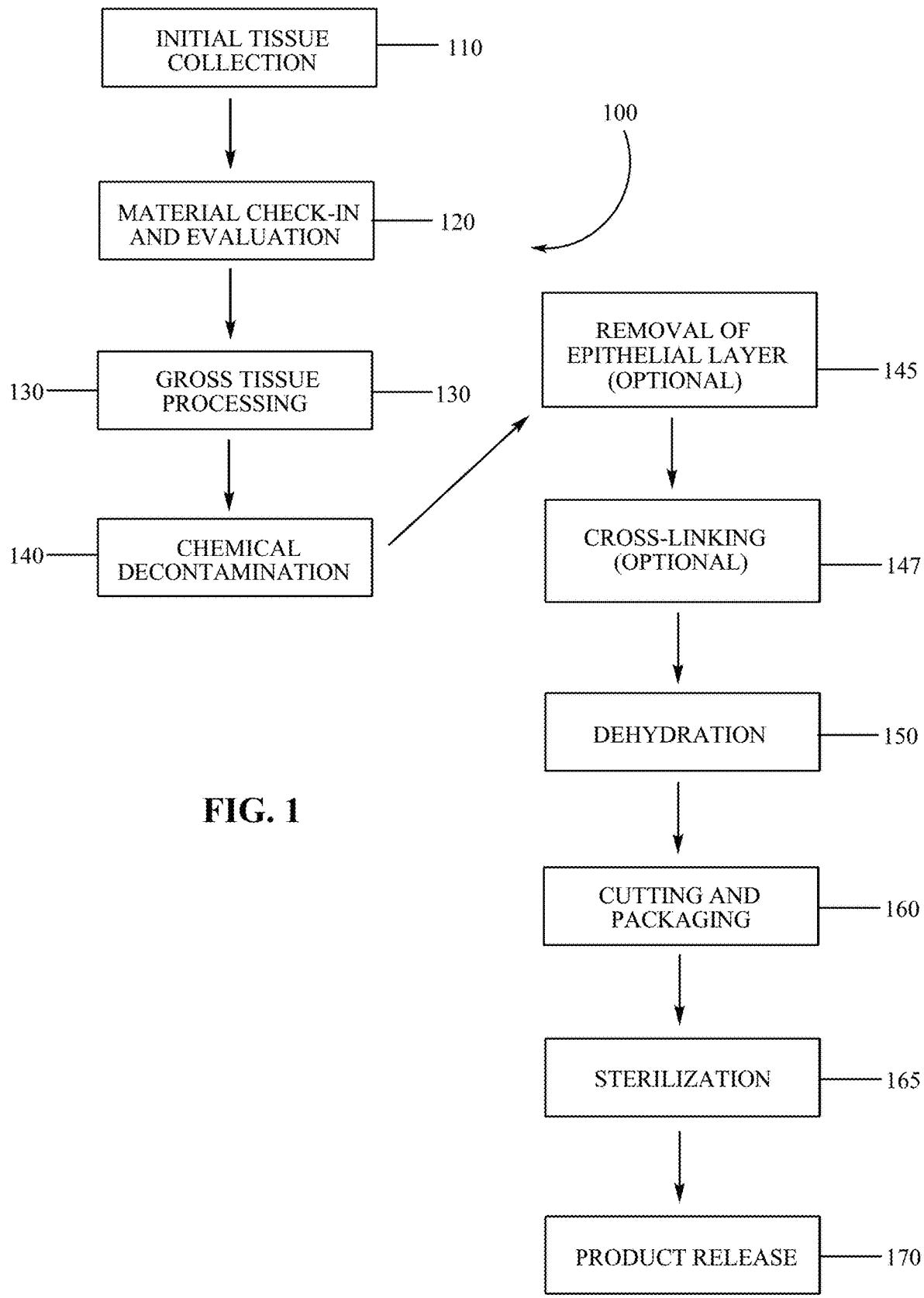
FIG. 1 is an overview flow chart of the process for making the tissue grafts described herein.

Described herein are reinforced tissue grafts derived from the placenta that possess good adhesion to biological tissues and are useful in would healing applications. FIG. 1 depicts an exemplary overview (100) and certain aspects of the steps to harvest, process, and prepare placental material for later use as a tissue graft. More detailed descriptions and discussion regarding each individual step will follow. Initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the amnion and chorion then takes place (step 130). Acceptable tissue is then decontaminated (step 140), followed by the optional steps of substantially removing the epithelium layer from the placental tissue (e.g., amnion or Wharton's jelly) to expose the basement membrane (step 145) and cross-linking of the placental tissue(s) (step 147) used to prepare the reinforced tissue grafts. The reinforced tissue graft is then prepared from the placental tissue and the graft is subsequently dehydrated (step 150), cut and packaged (step 160), sterilized using gamma radiation or electron beam radiation (step 165), and released (step 170) to the market for use by surgeons and other medical professionals in appropriate surgical procedures and for wound care. Each step is described in detail below.

Initial Tissue Collection (Step 110)

The components used to produce the tissue grafts are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

The methods described herein do not remove all cellular components in the amnion. This technique is referred to in the art as "decellularization." Decellularization generally involves the physical and/or chemical removal of all cells present in the amnion, which includes epithelial cells and fibroblast cells. For example, although the removal of epithelial cells is optional, the fibroblast layer present in the amnion stromal layer is intact, even if the intermediate tissue layer is removed. Here, fibroblast cells are present in the fibroblast layer.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below. Not wishing to be bound by theory, the removal of the intermediate layer can accelerate the drying of the tissue graft, particularly if multiple amnion membranes are used to produce the graft. The intermediate layer can be removed from the amnion prior contacting the amnion with the cross-linking agent or, in the alternative, can be removed after the amnion has been contacted with the cross-linking agent.

When the placental tissue is Wharton's jelly, the following exemplary procedure can be used. Using a scalpel or scissors, the umbilical cord is dissected away from the chorionic disk. Once the veins and the artery have been identified, the cord is dissected lengthwise down one of the veins or the artery. Once the umbilical cord has been dissected, surgical scissors and forceps can be used to dissect the vein and artery walls from the Wharton's jelly. Next, the outer layer of amnion is removed from the Wharton's jelly by cutting the amnion. Here, the outer membrane of the umbilical cord is removed such that Wharton's jelly is the only remaining component. Thus, the Wharton's jelly as used herein does not include the outer umbilical cord membrane and umbilical cord vessels. The Wharton's jelly can be cut into strips. In one aspect, the strips are approximately 1-4 cm by 10-30 cm with an approximate thickness of 1.25 cm; however, other thicknesses are possible depending on the application.

Chemical Decontamination (Step 140)

The amnion and chorion isolated above can be chemically decontaminated using the techniques described below. In one aspect, the amnion and chorion is decontaminated at room temperature. In one aspect, the amnion produced in step 130 can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hyperisotonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

The following exemplary procedure can be used when the placental tissue is Wharton's jelly. The Wharton's jelly is transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) with 18% NaCl. The container is sealed and placed on rocker plate and agitated for 60 to 90 minutes.

After the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1 to 10° C. for up to 24 hours.

The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After incubation, the jar is returned to the sterile field. The Wharton's jelly should have a cream white visual appearance with no evidence of brownish discoloration.

Removal of Epithelium Layer from Placental Tissue (Step 145)

In certain aspects, it is desirable, although optional, to remove the epithelium layer present on the placental tissue. In one aspect, the epithelium layer present on the amnion is substantially removed in order to expose the basement layer of the amnion. In another aspect, the epithelium layer present on the Wharton's jelly is substantially removed. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells.

The methods described herein, particularly steps 130 and 145, do not remove all cellular components in the amnion. This technique is referred to in the art as "decellularization." Decellularization generally involves the physical and/or chemical removal of all cells present in the amnion, which includes epithelial cells and fibroblast cells. Although step 145 does remove epithelial cells, the fibroblast layer present in the amnion stromal layer is intact (i.e., includes fibroblast cells), even after removal of the intermediate layer discussed in step 130.

Cross-Linking Step (step 147)

Depending upon the application of the tissue graft, one or more placental tissues use to produce the reinforced tissue graft can be optionally cross-linked. Not wishing to be bound by theory, the cross-linking of the placental tissue can modify the resorption properties of the placental tissue. For example, the placental tissue can be cross-linked in order to regulate the rate of release of growth factors present in the placental tissue. In other aspects, the cross-linked placental tissue can be sufficiently cross-linked in order to prevent bioactive agents (e.g., INFUSE®) from leaching out of the reinforced tissue graft. Here, the cross-linked placental tissue acts as a barrier.

The placental tissue grafts can be cross-linked using a number of techniques. In one aspect, cross-linking may be achieved by chemical, thermal, radiation, fibronectin, fibrinogen and/or hydrogel cross-linking methods. In other aspects, the placental tissue can be individually treated with a cross-linking agent prior to lamination and formation of the reinforced tissue graft. In general, the cross-linking agent is nontoxic and non-immunogenic. When two or more placental tissues are treated with the cross-linking agent, the cross-linking agent can be the same or different. In one aspect, the chorion and amnion can be treated separately with a cross-linking agent or, in the alternative, the chorion and amnion can be treated together with the same cross-linking agent. In certain aspects, the amnion or chorion can be treated with two or more different cross-linking agents.

The conditions for treating the placental tissue can vary. In one aspect, the amnion or chorion can be placed in a container holding an aqueous solution of the cross-linking agent. In one aspect, the concentration of the cross-linking agent is from 0.1 M to 5 M, 0.1 M to 4 M, 0.1 M to 3 M, 0.1 M to 2 M, or 0.1 M to 1 M. In another aspect, the placental tissue is treated with the cross-linking agent for 1 to 2 seconds up to 60 minutes. In a further aspect, the amnion or chorion are treated with the cross-linking agent at room temperature up to 50° C.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehydes such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the placental tissue to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof. Thus, in one aspect, the amnion or chorion include at least one cross-linker covalently attached to the membrane. In another aspect, a tissue graft includes an amnion and a chorion laminate, wherein the amnion and chorion are covalently attached to one another via a cross-linker.

The following procedure provides an exemplary method for treating the amnion and chorion with a cross-linking agent. The cleaned and decontaminated chorion and amnion are placed on the sterile field in the manufacturing hood. The tissue is transferred to a Nalgene jar containing a cross-linking agent, preferably 0.05 to 1 M D-ribose, preferably 0.2 M (3.01%) D-ribose, for 1 to 60 minutes, preferably 5 minutes. The tissues may be treated with the cross-linking agent either in separate containers or together in the same container. After the incubation, the tissue is removed from the solution and, optionally, allowed to dry.

Preparation of Micronized Compositions and Pharmaceutical Compositions Thereof

Once the placental tissue or components thereof as described above have been dehydrated individually or in the form of tissue graft, the dehydrated tissue(s) is micronized. The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, less than 200 µm, less than 100 µm, less than 50 µm, less than 25 µm, less than 20 µm, less than 15 µm, less than 10 µm, less than 9 µm, less than 8 µm, less than 7 µm, less than 6 µm, less than 5 µm, less than 4 µm, less than 3 µm, less than 2 µm, or from 2 µm, to 400 µm, from 25 µm to 300 µm, from 25 µm to 200 µm, or from 25 µm to 150 µm. In one aspect, the micronized composition has particles that have a diameter less than 150 µm, less than 100 µm, or less than 50 µm. In other aspects, particles having a larger diameter (e.g. 150 µm to 350 µm) are desirable. In all cases, the diameter of the particle is measured along its longest axis.

In one embodiment, the size of the particles may be reduced to nano-range. As one skilled in the art would understand, nanoparticles of placental components may be desirable for the increased density and/or increased release rate upon applying to the wound. Preferably, the particle size of the micronized particles is from about 0.05 µm to about 2 µm, from about 0.1 µm to about 1.0 µm, from about 0.2 µm to about 0.8 µm, from about 0.3 µm to about 0.7 µm, or from about 0.4 µm to about 0.6 µm. Alternatively, the particle size of the micronized particles is at least 0.05 µm, at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, or at least 1 µm. Alternatively, the particle size of the micronized particles is less than 1 µm, less than 0.9 µm, less than 0.8 µm, less than 0.7 µm, less than 0.6 µm, less than 0.5 µm, less than 0.4 µm, less than 0.3 µm, less than 0.2 µm, less than 0.1 µm, or less than 0.05 µm.

In other aspects, particles having a range of sizes and volumes are preferred as such particles will impart differential release rates into the wound. In one embodiment, particles having a range of mass to volume ratios can be prepared by either micronizing a mixture of a monolayer graft with multi-layer grafts (e.g., 2-10 layers) such that a range of graft sizes and volumes are provided. In another embodiment, particles of varying surface area to volume ratios of the same tissue material can be prepared by compressing the linear grafts into three-dimensional shapes of varying sizes (round, elliptical, oblong, etc.). As surface area to volume ratio is increased, particle dissipation increases due to the larger exposure area for endogenous enzymes, etc. This results in a faster rate of release of collagen types IV, V, and VII, cell-adhesion bio-active factors including fibronectin and laminins and other components of the micronized particles. On the other hand, as the surface area to volume ratio is decreased, particle dissipation decreases due to the smaller exposure area for endogenous enzymes, etc. This results in a slower rate of release of collagen types IV, V, and VII, cell-adhesion bio-active factors including fibronectin and laminins and other components of the micronized particles. In combination, the use of a layer of micronized particles having different surface area to volume ratios provides for a "time-release" mechanism whereby the benefits of the micronized graft are both immediate and prolonged.

In one embodiment, the surface area to volume ratio (based on a sphere having a range of diameters as described above) is between the range of about 0.06 µm to about $6 \times 10^4$ µm, about 0.06 µm to about $6 \times 10^3$ µm, about 0.06 µm to about $6 \times 10^2$ µm, or about 0.6 µm to about $6 \times 10^2$ µm.

Preparation of Reinforced Tissue Grafts and Dehydration (Step 150)

After the placental tissue has been prepared, a reinforced tissue graft is produced by laminating one or more placental tissues on each side of a biocompatible mesh. The biocompatible meshes useful herein generally have a plurality of pores. In one aspect, the biocompatible mesh can be made from a sheet or film of material containing circular, elliptical, or other shaped pores. Pores may be formed in the sheet or film by punching, drilling, milling, or other techniques known in the art. The pores should be of sufficient size to allow self-adherence of the placental tissue layers. In one aspect, the pore size can include diameters in the range from 200 to 4,000 microns and can be spaced from 1,000 to 4,500 microns apart as measured from center of pore to center of pore. The thickness of the sheet or film can range from 300 to 2,000 microns. The pores in the biocompatible mesh may be chamfered, radiused, or other method commonly known to those skilled in the art in order to prevent the edges of the pores from cutting the placental tissue.

In other aspects, the mesh can be a textile mesh made by weaving, knitting, felting, or other textile methods known in the art using fibers, wires, or yarns of a biocompatible material in order to create a textile mesh with pores. In one aspect, the pore size can range from 0.5 mm to 3 mm in diameter. In another aspect, the thickness of the textile mesh can range from 300 to 2000 microns.

In one aspect, the biocompatible mesh can be made from non-resorbable materials including but not limited to biocompatible metals such as titanium alloys, stainless steel, cobalt-chromium alloys, and nickel-titanium alloys. In another aspect, the layer of biocompatible mesh can be made from non-resorbable polymeric materials, including but not limited to, thermoplastic resins, polyethylenes, ultra-high weight molecular weight polyethylene, high molecular weight polyolefins, uncoated monofilament polypropylene, polyether ether ketone, polyethylene terephthalate, polytetrafluoroethylene, expanded polytetrafluoroethylene, nylon, any polymer or aliphatic hydrocarbons containing one or more double bonds, any other appropriate porous materials, or any other appropriate porous material that can be bent or otherwise formed into a shape.

In another aspect, the biocompatible mesh can be composed of a synthetic or biological resorbable polymeric material including but not limited to polyglycolic acid, poly-L-lactic acid (PLLA), poly-D,L-lactic acid (PDLA), trimethylenecarbonate (TMC), poly-ε-caprolactone, poly-P-dioxanone, copolymers of lactide and glycolide (PLGA), polyhydroxy-3-butyrate, collagen, hyaluronic acid, silk, biocellulose, other protein-based polymers, polysaccharides, poly(DTE carbonate), polyarylates, blends of PLLA, PLDA, or PLGA with TMC and other combinations of these polymers.

The reinforced tissue grafts are generally a sandwich structure composed of one or more placental tissues laminated on each side of the biocompatible mesh. The reinforced tissue grafts can have from 1 to 10 placental tissues laminated on each side of the biocompatible mesh. Furthermore, the placental tissue can be any combination of tissues (e.g., amnion, chorion, Wharton's jelly, etc.). Finally, the placental tissue can be optionally modified (e.g., removal of the epithelium cells and/or intermediate layer) and/or cross-linked using the techniques described above.

In one aspect, the biocompatible mesh as described herein can be either structurally homologous or heterologous in its configuration, wherein a structurally homologous biocompatible mesh is wholly composed from placental tissue, including, but not limited to, be amnion, chorion, Wharton's jelly and the like, and wherein a structurally heterologous biocompatible mesh is composed from placental tissue that can be any combination of placental tissues as described herein.

In other aspects, the biocompatible mesh as described herein can be coated with micronized placental tissue to provide a further amount of placental tissue for use as described herein. Micronized placental tissue can be prepared by using instruments known in the art and as further described herein.

In another aspect, the micronized placental tissue can be injected into a tissue graft or applied directly to a wound site as a jetted solution using a needle-free transdermal transport device. Jetting techniques using needle-free transdermal transport devices are known by those of skill in the art. In certain aspects, jetting techniques may be used as a substitute method for applying micronized placental tissue. Alternatively, jetting techniques may be used to supplement additional micronized placental tissue to the tissue graft or wound site to enhance wound healing and other medical applications. In certain other aspects, the micronized placental tissue may be provided in any suitable medium depending on the jetting technique being used, including, but not limited to, solutions, suspensions and powders.

In another aspect, the micronized placental tissue may be applied to the surface of a membrane by first depositing the micronized placental tissue onto a non-stick surface such as Teflon® and subsequently thereafter contacting the interior surface of the membrane with the deposited micronized placental tissue to absorb the micronized placental tissue onto the interior surface of the membrane. In this aspect, the non-stick surface can be sterilized according to conventional methods, prior to deposition of the micronized placental tissue. In certain aspects, the membrane or graft can be provided in a wet form to facilitate adhesion of the micronized placental tissue to the membrane. In another aspect, a second membrane can be later applied onto the first membrane containing the micronized placental tissue to produce a tissue graft.

In one aspect, the reinforced tissue graft includes:
a first membrane comprising a placental tissue having a first side and a second side;
a biocompatible mesh having a first side and a second side, wherein the first side of the biocompatible mesh is adjacent to the second side of the first membrane; and
a second membrane comprising a placental tissue having a first side and a second side, wherein the first side of the second membrane is adjacent to the second side of the biocompatible mesh.

Figure 3:
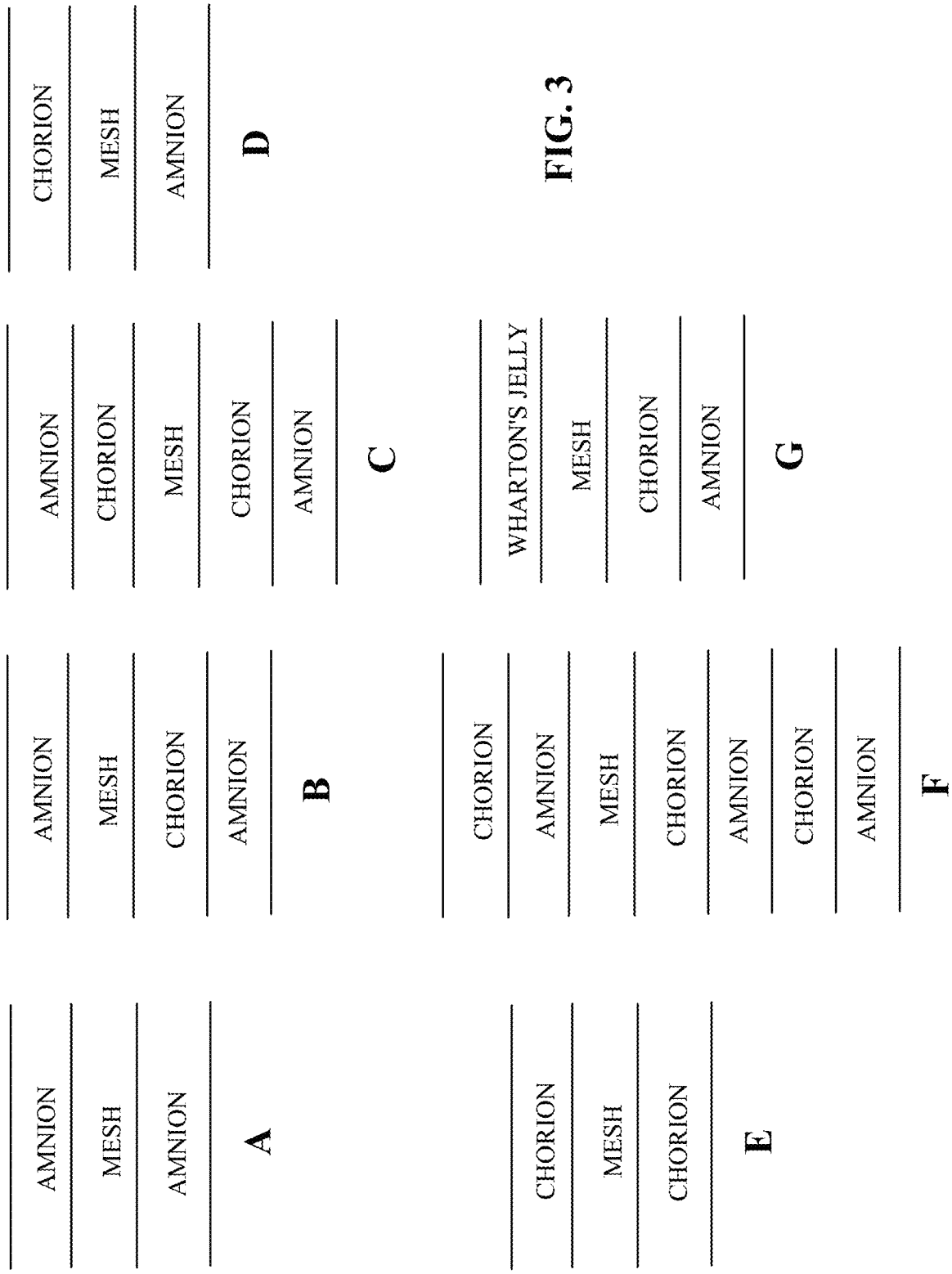
FIG. 3 depicts several embodiments of the reinforced tissue grafts described herein.

The reinforced tissue grafts can be configured in a number of different configurations depending upon the application of the tissue graft. In one aspect, the first membrane comprises amnion, chorion, or a laminate comprising one or more layers of amnion with one or more layers of chorion. In another aspect, the second membrane comprises amnion, chorion, or a laminate comprising one or more layers of amnion with one or more layers of chorion. A number of different configurations of the reinforced tissue graft are depicted in FIG. 3 (A-G).

In one aspect, the first membrane comprises modified amnion wherein the modified amnion comprises a first side which is an exposed basement membrane and a second side, and wherein the second side of the modified amnion is adjacent to the first side of the biocompatible mesh. In another aspect, the first membrane comprises modified amnion wherein the modified amnion comprises a first side which is an exposed basement membrane and a second side which is an exposed fibroblast layer comprising fibroblast cells, and wherein the second side of the modified amnion is adjacent to the first side of the biocompatible mesh.

In another aspect, the second membrane comprises an amnion/chorion laminate, wherein the chorion is adjacent to the second side of the biocompatible mesh.

In a further aspect, the second membrane comprises an amnion/chorion laminate, wherein the chorion is adjacent to the second side of the biocompatible mesh, the amnion comprises an epithelium layer and an intermediate layer, and the chorion is adjacent to the intermediate layer.

In a further aspect, the second membrane comprises an amnion/chorion laminate, wherein the chorion is adjacent to the second side of the biocompatible mesh, the amnion comprises a modified amnion comprising an exposed basement membrane and an intermediate layer, and the chorion is adjacent to the intermediate layer.

In a further aspect, the second membrane comprises an amnion/chorion laminate, wherein the chorion is adjacent to the second side of the biocompatible mesh, the amnion comprises a modified amnion comprising an exposed basement membrane and an exposed fibroblast layer comprising fibroblast cells, and the chorion is adjacent to the exposed fibroblast layer.

In one aspect, the reinforced tissue graft is composed of a layer of amnion (i.e., first membrane) where the epithelium layer has been substantially removed in order to expose the basement layer to host cells, a biocompatible mesh, and a layer of amnion (i.e., second membrane) (with or without the epithelia cells) (FIG. 3A). Here, the exposed basement layer is not adjacent to the biocompatible mesh.

In another aspect, the reinforced tissue graft is composed of a layer of amnion (with layer of epithelial cells), a layer of chorion, a layer of biocompatible mesh, and a layer of amnion (with or without the epithelial cells). In this aspect, the layer of amnion and chorion collectively are the first membrane (FIG. 3B). Here, the exposed basement layer or the epithelial layer of the amnion is not adjacent to the biocompatible mesh.

In another aspect, the reinforced tissue graft is composed of layer of amnion where the epithelium layer has been substantially removed in order to expose the basement layer to host cells, a layer of chorion, a second layer of amnion (with layer of epithelia cells), a second layer of chorion, a layer of biocompatible mesh, a layer of amnion (with layer of epithelia cells), and a layer of chorion (FIG. 3F).

In a further aspect, the reinforced tissue graft is composed of a layer of amnion where the epithelium layer has been substantially removed in order to expose the basement layer to host cells, a layer of chorion, a layer of biocompatible mesh, and a layer of Wharton's jelly (FIG. 3G). Here, the exposed basement layer is not adjacent to the biocompatible mesh.

In another aspect, the reinforced tissue graft is composed of a layer of Wharton's jelly where the outer layer of epithelium is removed, a layer of biocompatible mesh, a layer of chorion, and a layer of amnion where substantially all of the epithelium cells are removed to expose the basement membrane (FIG. 3G). Here, the side of the Wharton's jelly where the epithelial cells have been removed are not adjacent to the biocompatible mesh. Additionally, the exposed basement membrane of the amnion is not adjacent to the chorion.

In certain aspects, a bioactive agent can be added to the placental tissue prior to and/or after lamination and production of the reinforced tissue graft. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the reinforced tissue graft with bioactive agent to the region of interest, the bioactive agent is delivered to the region over time. Thus, the reinforced tissue grafts described herein are useful as delivery devices of bioactive agents and other pharmaceutical agents when administered to a subject.

Release profiles can be modified based on, among other things, the degree of cross-linking in the placental tissue grafts used to prepare the reinforced tissue graft. In certain aspects, the tissue grafts described herein are useful in wound healing applications where it is desirable to keep a bioactive agent localized in the wound so that the wound heals quicker. Additionally, if the bioactive agent is toxic when released systemically throughout the subject, the reinforced tissue grafts described herein can provide an effective, impermeable barrier that prevents the bioactive agent from migrating from the wound. For example, the placental tissue can be sufficiently cross-linked in order to prevent a bioactive agent such as INFUSE® from leaching out of the reinforced tissue graft. Here, the cross-linked placental tissue in the reinforced tissue graft acts as a barrier.

The preparation of the reinforced tissue grafts generally involves the sequential layering of placental tissue on the biocompatible mesh. In one aspect, one or more placental tissues (i.e., the first membrane) can be placed on the surface of a drying fixture. Next, the biocompatible mesh is applied to the first membrane, with the subsequent layering of one or more additional placental tissues (i.e., the second membrane) on the biocompatible mesh.

In certain aspects, adhesives such as, for example fibrin glue and hydrogels, can be used to adhere the placental tissues together as well as to the biocompatible mesh. Fibrin glue is prepared from pooled blood and has the potential to transmit disease. At this time, the application of fibrin glue to seal dural tears constitutes off label use. Synthetic hydrogels such as the DuraSeal Spine Sealant System (Confluent Surgical Inc., Waltham, Mass.) consist of two components (polyethylene glycol ester and trilysine amine) and a delivery system which polymerize at the defect site to form a seal. As the hydrogel swells to up to 50% in size during polymerization, neural compression may occur.

The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Figure 2:
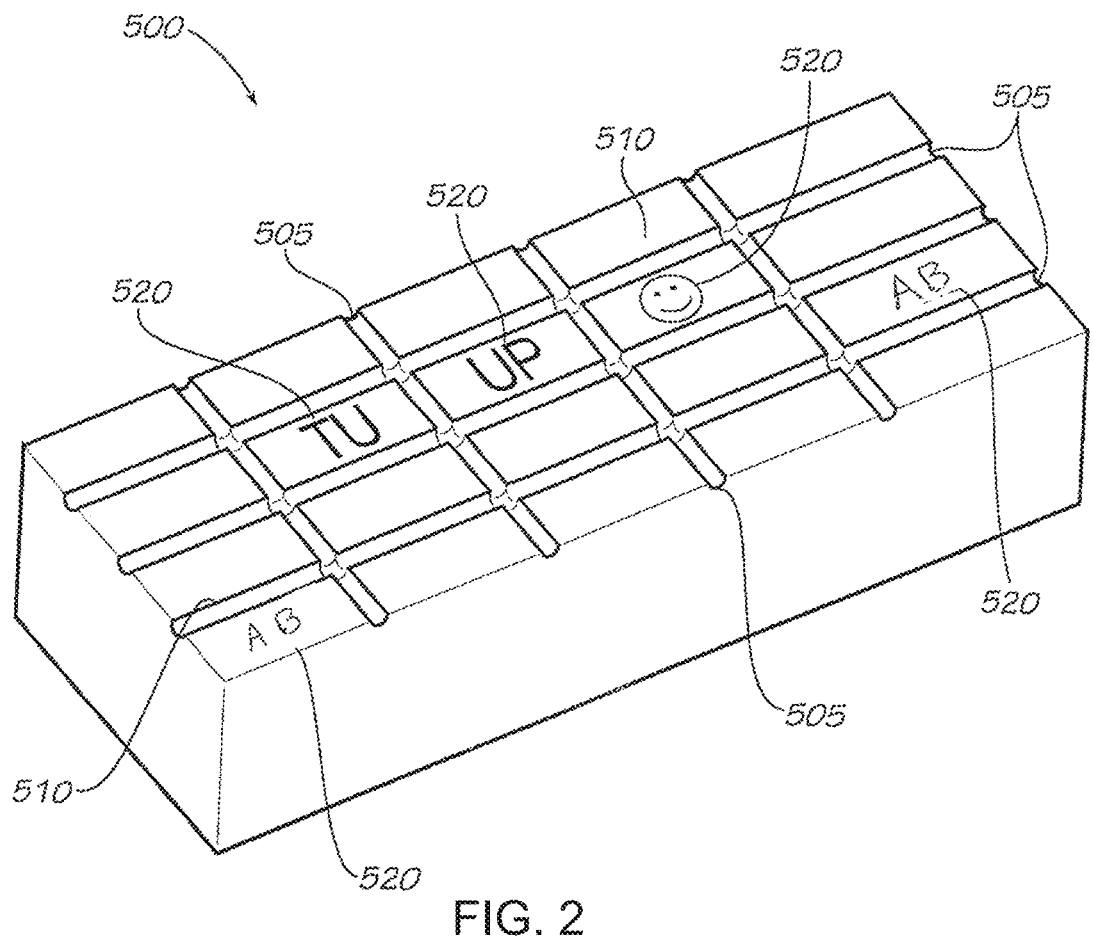
FIG. 2 is a perspective view of an exemplary drying fixture for making the tissue grafts described herein.

In one aspect, similar to that shown in FIG. 2, the receiving surface of the drying fixture 500 has grooves 505 that define the product spaces 510, which are the desired outer contours of the tissue after it is cut and of a size and shape that is desired for the applicable surgical procedure in which the tissue will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another embodiment, instead of having grooves to define the product spaces, the drying fixture has raised ridges or blades.

Within the "empty" space between the grooves or ridges, the drying fixture can include a slightly raised or indented texture in the form of an indicia 520 (e.g., a text, logo, name, or similar design). Here, the indicia can be seen by the naked eye (with or without corrective lenses) and not by magnification techniques. This textured text, logo, name, or design can be customized. When dried, the tissue will mold itself around the raised texture or into the indented texture—essentially providing a label within the tissue itself. Preferably, the texture/label can be read or viewed on the tissue graft in only one orientation so that, after drying and cutting, an end user (typically, a clinician) of the dried tissue will be able to tell the stromal side from the basement side of the dried tissue. The reason this is desired is because, during a surgical procedure, it is desirable to place the allograft in place, with amnion basement side down or adjacent the native tissue of the patient receiving the allograft. FIG. 2 illustrates a variety of marks, logos, and text 520 that can be included within the empty spaces 510 of the drying fixture 500. Typically, a single drying fixture will include the same design or text within all of the empty spaces; however, FIG. 2 shows, for illustrative purposes, a wide variety of designs that can be included on such drying fixtures to emboss each graft.

In one aspect, after the reinforced tissue graft has been produced and prior to dehydration, pressure can be applied to the tissue graft such that the first and second membrane are pressed into the pores of the biocompatible mesh and come into contact with one another. In one aspect, a dry roller is rolled over the reinforced tissue graft. In another aspect, the biocompatible mesh is pressed into the placental allograft using a mechanical press that only comes into contact with the biocompatible mesh. In this aspect, the biocompatible mesh is pressed into the first membrane, where the second membrane is subsequently applied on the biocompatible mesh. In another aspect, a wetted plate with raised knobs can be placed on the reinforced tissue graft and pressed down such that the layers of placental tissue come into contact with one another.

Once the reinforced tissue graft is produced, the reinforced tissue graft is dehydrated. In one aspect, the drying fixture with the reinforced tissue graft is placed in a freeze-dryer. The use of the freeze-dryer to dehydrate the tissue grafts can be more efficient and thorough compared to other techniques such as thermal dehydration. In general, it is desirable to avoid ice crystal formation in the placental tissue grafts as this may damage the extracellular matrix in the tissue graft. By chemically dehydrating the placental tissue prior to freeze-drying, this problem can be avoided.

In another aspect, the dehydration step involves applying heat to the tissue graft. In one aspect, the drying fixture with the reinforced tissue graft is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed at 45 minutes at a temperature of approximately 45 degrees Celcius to dry the tissue sufficiently but without over-drying or burning the tissue graft. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Figure 4:
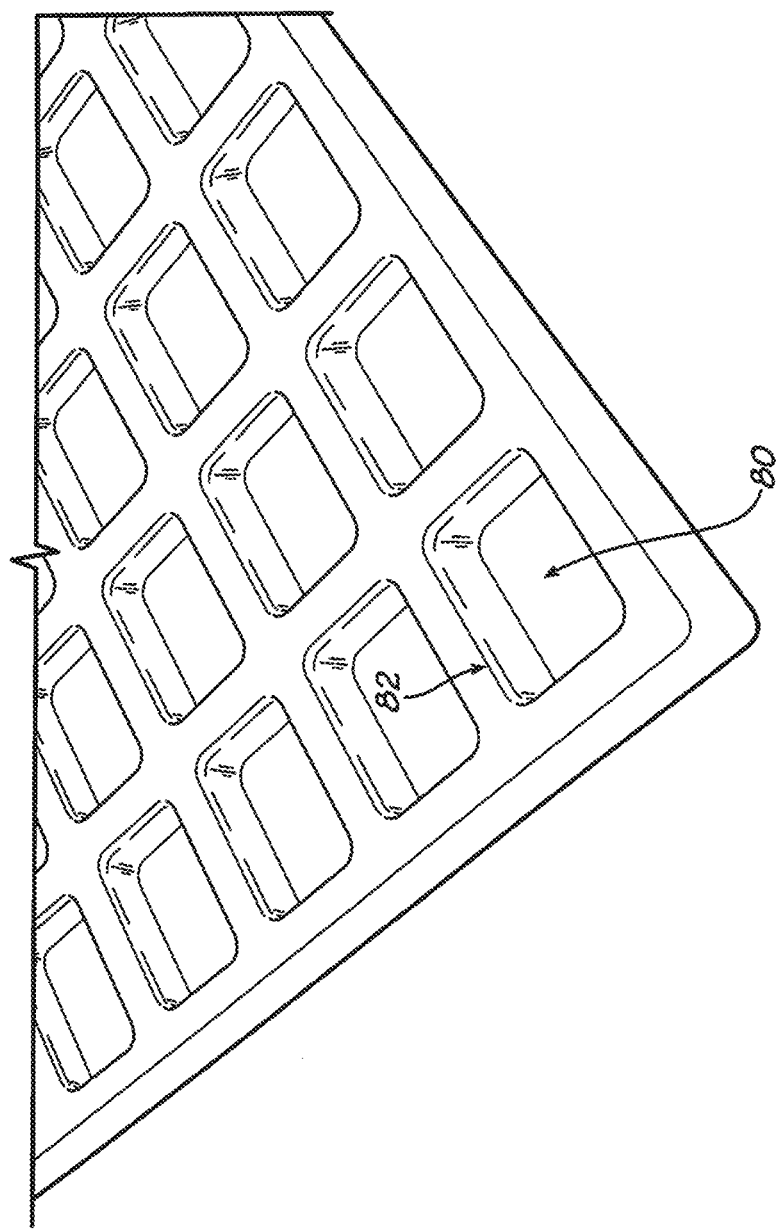
FIG. 4 shows an exemplary drying fixture and drying rack useful in preparing tissues grafts described herein.

In certain aspects, once the reinforced tissue graft has been applied to the drying fixture, a drying frame can be applied over the graft. This feature is depicted in FIG. 4, where the drying rack 82 is placed on top of drying fixture 80. The drying frame holds the graft in place. Additionally, the drying frame allows the entire sheet of tissue graft to dry completely without lifting, which results in increased yields.

In another aspect, the reinforced tissue graft is dehydrated by chemical dehydration followed by freeze-drying. In one aspect, the chemical dehydration step is performed by contacting the placental tissue independently or as a laminate with a polar organic solvent for a sufficient time and amount in order to substantially (i.e., greater than 90%, greater than 95%, or greater than 99%) or completely remove residual water present in the placental tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the reinforced tissue graft is freeze-dried in order to remove any residual water and polar organic solvent. In one aspect, the reinforced tissue graft can be laid on a suitable drying fixture prior to freeze-drying.

In another aspect, the placental tissue grafts described herein can be dehydrated using an innovative dehydration device which enhances the rate and uniformity of the dehydration process. In one embodiment, the drying time can be accelerated by up to 40% in one configuration of the dehydration device in comparison to conventional drying ovens. In certain aspects, the placental tissue graft is placed onto a drying fixture described herein and the drying fixture with tissue graft is inserted into the dehydration device for performing the dehydration process. In other aspects, multiple placental tissue grafts can be placed onto the drying fixture to dry more than one placental tissue grafts in the dehydration device at the same time. Although the dehydration device is useful in dehydrating the tissue grafts described herein, they can be used for dehydrating objects other than placental tissue.

FIGS. 8-11 show an innovative dehydration device 900 according to an example embodiment that is well-suited for use in the herein-described dehydration processes. The dehydration device 900 includes a drying housing 902, and inflow plenum 904, and outflow plenum 906, an air-moving assembly 908, an air-heating assembly 910, and a control system 912.

Figure 8:
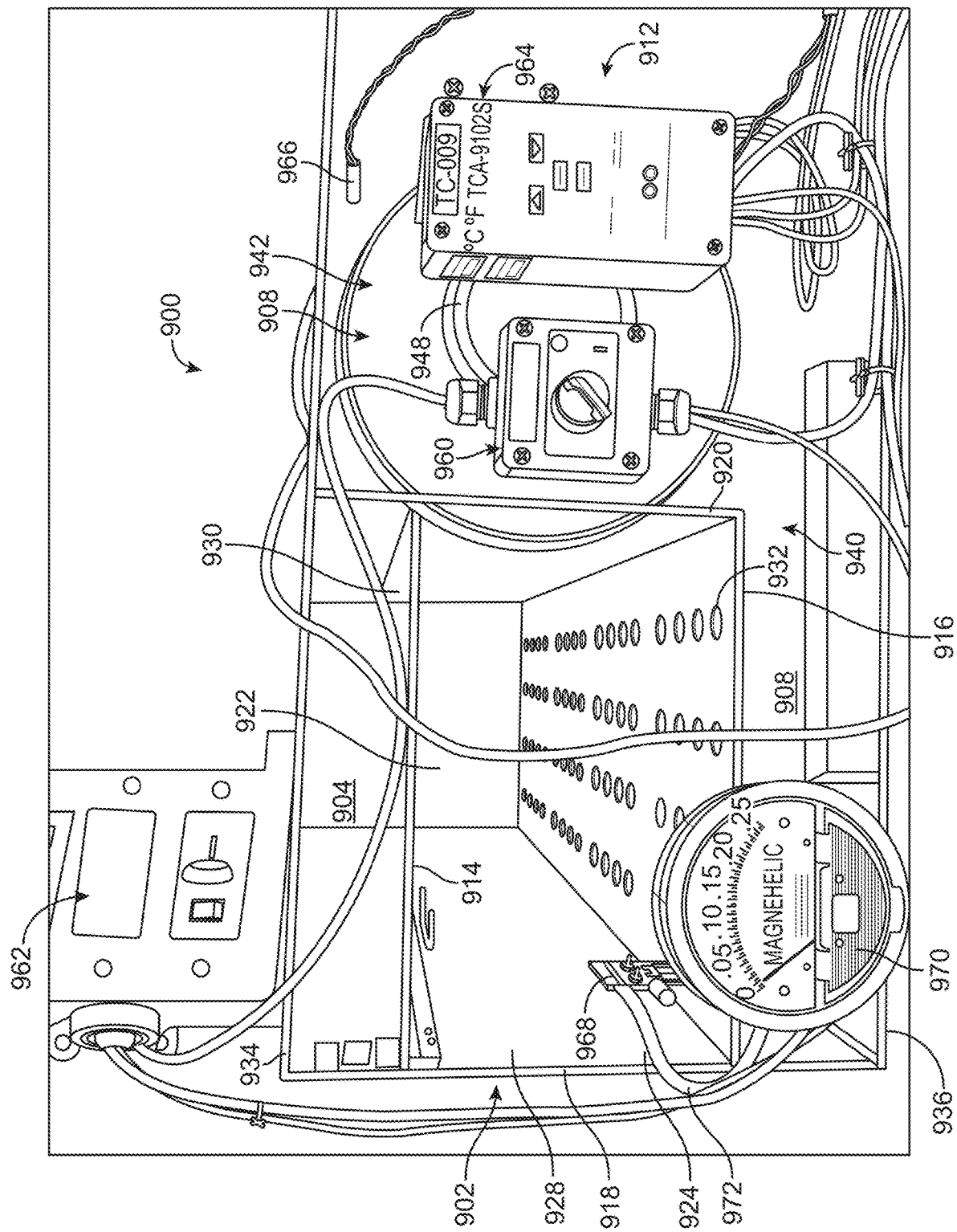
FIG. 8 shows a forward perspective view of a dehydration device as described herein.
Figure 9:
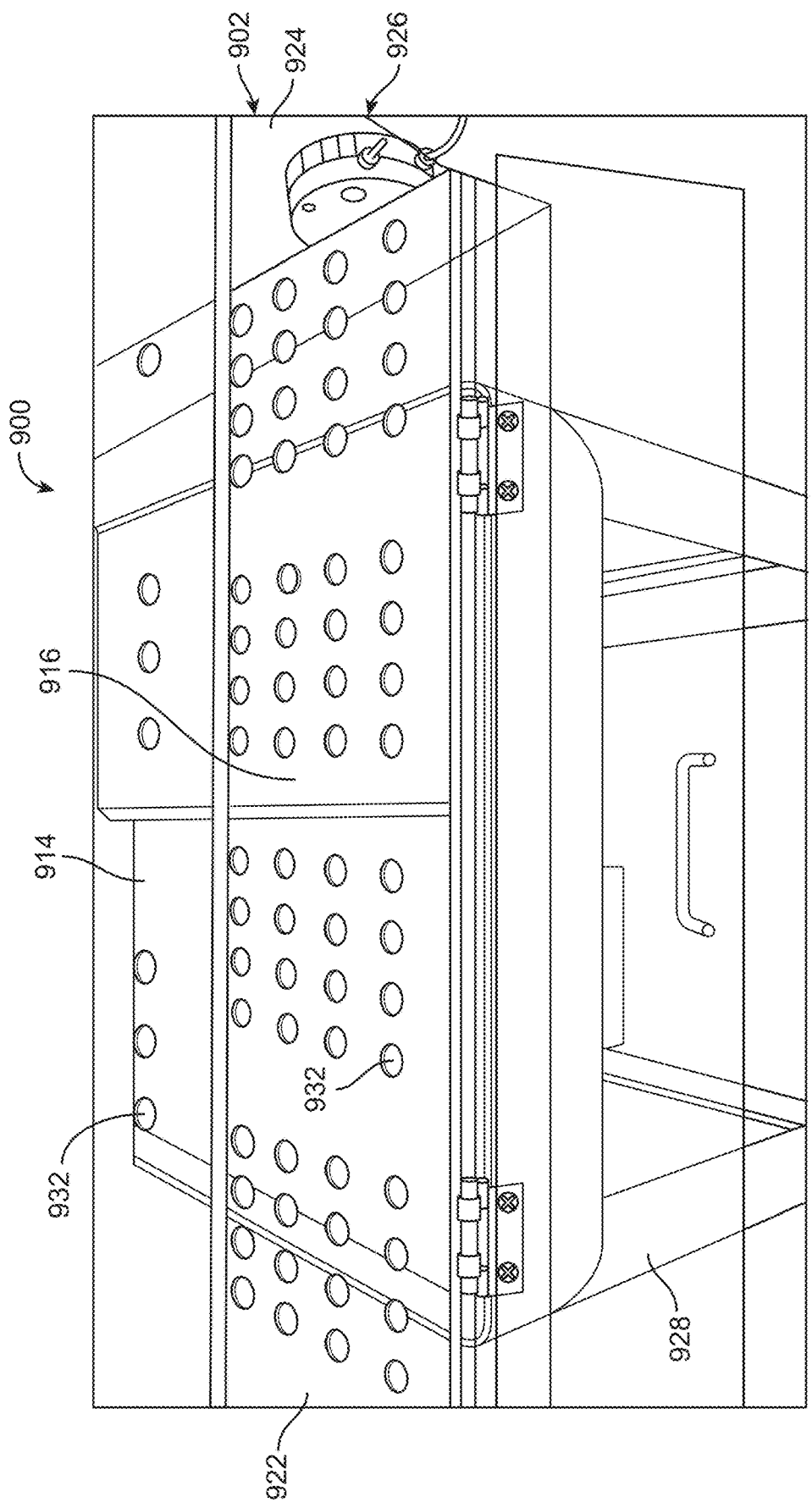
FIG. 9 shows an overhead perspective view of a dehydration device as described herein.
Figure 10:
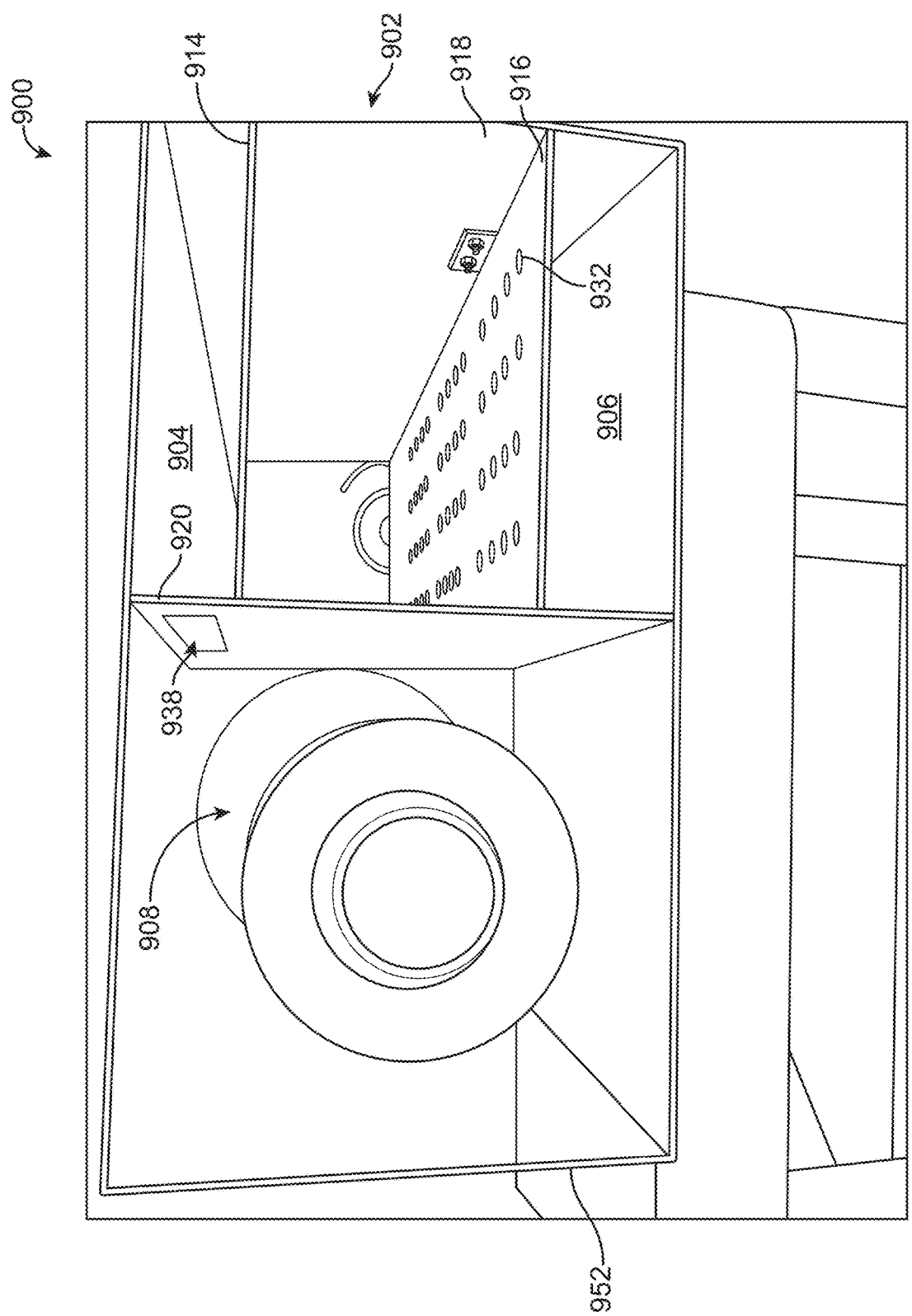
FIG. 10 shows a side perspective view of a dehydration device as described herein.
Figure 11:
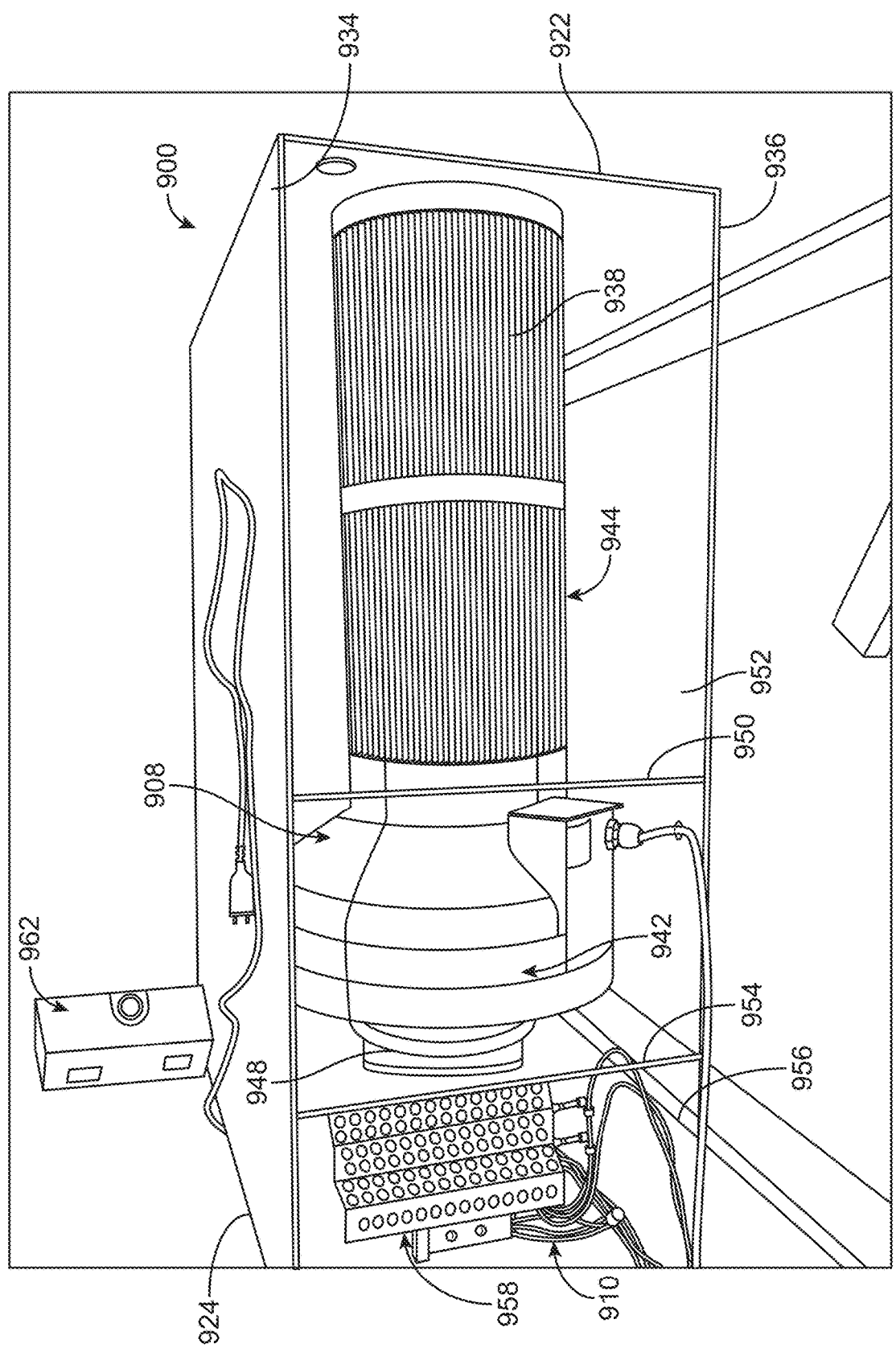
FIG. 11 shows a back perspective view of a dehydration device as described herein.

The drying housing 902 defines a drying chamber into which the placental tissue (e.g., ton a drying fixture) is placed for drying during the dehydration process. In typical embodiments, the drying housing 902 (and thus the drying chamber it defines) is formed by six generally planar walls arranged together in a generally rectanguloid shape. In other embodiments, the drying housing 902, and/or the drying chamber it defines, has a different regular or irregular shape such as spherical or ellipsoidal. In the depicted embodiment, the drying housing 902 is formed by top and bottom opposing walls 914 and 916, first and second opposing sidewalls 918 and 920, and first and second opposing endwalls 922 and 924. The drying housing 902 includes a doorway opening 926 and a door 928 (e.g. hingedly coupled to the housing and including a pull-knob) in at least one of the walls (e.g., sidewall 918) for inserting the placental tissue on a fixture for dehydration and then removing the dried tissue. (FIG. 8 shows the door 928 in a closed position and FIG. 9 shows it in an opened position.) The walls of the housing 902 are typically made of a material selected for rigidity, strength, and heat-resistance, for example an acrylic (e.g., PLEXIGLAS), glass, ceramic, or other polymeric material.

At least two of the walls of the housing 902 each define at least one respective aperture through which air can flow. In the depicted embodiment, for example, the top and bottom opposing walls 914 and 916 have an array of inflow and outflow apertures 930 and 932, respectively, formed in them. In such embodiments, the placental tissue graft (e.g., on a fixture) is placed into the drying chamber supported by the bottom wall 916 and typically at least partially covering at least one of the outflow apertures 932. The size, shape, and position of the apertures 930 and 932 are selected based on the range of operating parameters (volumetric flow rate, flow pattern, temperature, pressure, time/duration, etc. of the air flowing through the housing 902) of the device 900 as may be desired for drying the placental tissue. Thus, the apertures 930 and 932 can be circular, aligned with corresponding apertures in the opposing wall, arranged in segmented rows and/or columns, and arranged uniformly (for a generally uniform temperature and drying effect across the chamber), as depicted. In other embodiments, the apertures have a non-circular shape (e.g., polygonal or elliptical), have differing sizes (e.g., interspersed larger and smaller apertures, or differing inflow and outflow aperture sizes), and/or are formed in an irregular and/or non-aligning pattern. And in yet other embodiments, the apertures are formed in only one of the walls, more than two of the walls, or the opposing sidewalls 918 and 920 (instead of or in addition to the opposing top and bottom walls 914 and 916), and/or the inflow plenum 904 can be eliminated and piping coupled between the air-moving assembly 908 and an inflow one of the walls (e.g., top wall 914).

The inflow plenum 904 and the outflow plenum 906 are positioned in communication with the inflow apertures 930 and the outflow apertures 932, respectively. The plenums 904 and 906 help generate an even distribution of the pressure, flow, and temperature of the air flowing through the drying housing 902. In the depicted embodiment, the inflow plenum 904 is formed by first vertically upward extensions of the opposing sidewalls 918 and 920 and the opposing endwalls 922 and 924 together with the housing top wall 914 and an opposing inflow-plenum top wall 934. And the outflow plenum 906 is formed by second vertically downward extensions of the opposing sidewalls 918 and 920 and the opposing endwalls 922 and 924 together with the housing bottom wall 916 and an opposing outflow-plenum bottom wall 936. In other embodiments, the plenums 904 and 906 are eliminated and the air-moving assembly 908 is piped directly to the drying housing 902.

The inflow plenum 904 and the outflow plenum 906 include at least one inflow port 938 and outflow port 940, respectively. In the depicted embodiment, the inflow port 938 is defined by a generally rectangular opening formed in the sidewall 920 at an upper portion thereof and at a first/distal portion thereof, and the outflow port 940 is defined by a generally rectangular gap in the same sidewall (i.e., an absence of the second extension of the wall) but at a lower portion thereof and at a second/proximal portion thereof. In this way, the air flows laterally into the inflow plenum 904 at the first/distal and upper portion of the dehydration device 900 and then distributes proximally within the inflow plenum. Then the air flows down through the inflow apertures 930, down through and across the drying chamber, down through the outflow apertures 932, down into the outflow plenum 906, and laterally out at the second/proximal and lower portion of the device 900. The plenums 904 and 906 provide for generally evenly distributed airflow across the tissue even though the air enters the inflow plenum at the first/distal portion of the dehydration device 900 and exits the outflow plenum at the second/proximal portion (while flowing from top to bottom through the drying chamber). Alternatively, the inflow and outflow ports 938 and 940 can be positioned to provide airflow from bottom to top (and/or from side to side) through the drying chamber, and/or they can have other regular or irregular shapes such as circular.

The air-moving assembly 908 can be of a commercially available type for use in sterile/clean-air environments such as medical laboratories. Typically, the air-moving assembly 908 includes a blower 942 and a filter 944. The blower 942 can be of a conventional type, for example including an electric motor and a fan enclosed within a housing. And the filter 944 can be of a conventional type, for example a cylindrical HEPA air filter with an internal bore. Typically, such filter 944 mounts to and extends from the blower 942, and air flows axially through the internal bore and radially outward through the filter media.

The dehydration device 900 can be configured in a closed airflow loop (to re-circulate the air) or in an open loop (to provide fresh intake air). In closed-loop designs, an air outlet surface 946 of the filter 944 is in sealed communication with the inflow port 938 of the inflow plenum 904, and an air intake 948 of the blower 942 is in sealed communication with the outflow port 940 of the outflow plenum 906. In the depicted embodiment, for example, the air outlet surface 946 of the filter 944 is enclosed in a first/distal delivery chamber formed by lateral extensions of the plenum top and bottom walls 934 and 936, a lateral extension of the first/distal endwall 922 and an opposing second/proximal delivery-chamber endwall 950, and the second sidewall 920 and an opposing delivery-chamber sidewall 952. And the air intake 948 of the blower 942 is sealed communication with a second/proximal return chamber formed by lateral extensions of the plenum top and bottom walls 934 and 936, a lateral extension of the second/proximal endwall 924 and an opposing first/distal return-chamber endwall 954 (having an return opening in sealed communication with the blower air intake), and the second sidewall 920 and an opposing return-chamber sidewall 956. A sidewall section can be provided to enclose the blower 942 or this can be left out to allow ambient air exposure to prevent the blower from overheating. In the depicted embodiments, the result is that the outer walls of the dehydration device 900 form a rectanguloid structure. In other embodiments, the air outlet surface 946 of the filter 944 is piped to the inflow port 938 of the inflow plenum 904 and the air intake 948 of the blower 942 is piped to the outflow port 940 of the outflow plenum 906.

The air-heating assembly 910 includes at least one heating element 958, which can be of a conventional type such as a commercially available electric-resistance heating element. The heating element 958 is typically positioned adjacent the air intake 948 of the blower 942, for example mounted on a bracket within the return chamber, as depicted.

The control system 912 includes conventional controls for controlling the operating parameters (airflow rate, pressure, temperature, time/duration, etc.) of the dehydration device 900. Such conventional controls typically include a main power switch 960 that is wired to provide power to a variable resistance device 962 and a control unit 964. The main power switch 960 is wired to a power source such as conventional 120/240 line voltage. The variable resistance device 962 (e.g., a rheostat) is wired (for power and control) to the heating element 958 (e.g., via the control unit 964) for temperature control. At least one heat sensor 966 is positioned in the return chamber and wired to the control unit 964 to provide an input for use in temperature control. And the control unit 964 is wired (for power and control) to the blower 942 for controlling the volume flow rate (and thus also the pressure) and the time/duration of the dehydration cycle. In addition, typical embodiments such as that depicted include a pressure sensor 968 in (or at least exposed to) the drying chamber, a pressure gauge display 970 (e.g., mounted to the drying housing 902), and a fluid connection 972 (e.g., tubing) interconnecting the two parts.

Cutting & Packaging (Step 160)

Once the reinforced tissue graft has been adequately dehydrated, the tissue graft is then ready to be cut into specific product sizes and appropriately packaged for storage, terminal sterilization, and later surgical use. In one aspect, the Tyvek bag containing the dehydrated tissue is placed back into the sterile/controlled environment. The number of grafts to be produced is estimated based on the size and shape of the tissue on the drying fixture(s). An appropriate number of pouches, one for each tissue graft, is also introduced into the sterile/controlled environment. The drying fixture(s) are then removed from the Tyvek bag.

If the drying fixture has grooves, then the following exemplary procedure can be used for cutting the tissue graft into product sizes. If the drying fixture is configured in a grid pattern, a #20 or similar straight or rolling blade is used to cut along each groove line in parallel. Next, all lines in the perpendicular direction are cut. Alternatively, if the drying fixture has raised edges or blades, then the following procedure can be used for cutting the tissue graft into product sizes. A sterile roller is used to roll across the drying fixture.

Sufficient pressure must be applied so that the dehydrated tissue graft is cut along all of the raised blades or edges of the drying fixture.

After cutting, each tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate tissue graft.

Each tissue graft is then given a final inspection to confirm that there are no tears or holes, that the product size (as cut) is within approximately 1 millimeter (plus or minus) of the specified length and width size and within approximately 250 microns (plus or minus) thick for that particular graft, that there are no noticeable blemishes or discoloration of the tissue graft, and that the textured logo or wording is readable and viewable through the "inner" pouch.

To the extent possible, oxygen is removed from the inner pouch before it is sealed. The inner pouch can be sealed in any suitable manner; however, a heat seal has shown to be effective. In one aspect, after packaging, the product is terminally sterilized by radiation, using gamma or electron beam sterilization with a target dose of, for example, 17.5 kGy. Next, each inner pouch is separately packaged in an "outer" pouch for further protection, storage, and shipment.

It should be noted that none of the steps described above involve freezing the tissue graft to kill unwanted cells, to decontaminate the tissue graft, or otherwise to preserve the tissue graft. The dehydrated tissue grafts described herein are designed to be stored and shipped at room or ambient temperature without need for refrigeration or freezing.

Product Release (Step 170)

Before the reinforced tissue graft is ready for shipment and release to the end user, all documentation related to the manufacture, recovery and donor eligibility are reviewed and deemed acceptable by the quality assurance department and the medical director.

Appropriate labeling and chain of custody is observed throughout all of the above processes, in accordance with accepted industry standards and practice. Appropriate clean room and sterile working conditions are maintained and used, to the extent possible, throughout the above processes.

II. Applications of Reinforced Tissue Grafts

Due to the enhanced adhesive nature structural features of the reinforced tissue grafts described herein, the grafts can be used in numerous medical applications involving wound healing in a subject. In one aspect, when the placental tissue is cross-linked, the cross-linking groups covalently attached to the tissue graft can facilitate the non-enzymatic cross-linking of proteins within the graft such as, for example, collagen, and other proteins present in a biological tissue. In one aspect, cross-linked tissue grafts described herein can cross-link (i.e., form a covalent bond) with dura matter. In other aspects, the tissue grafts described herein can adhere to tendons, ligaments, muscle, and other body tissue. The tissue grafts described herein are useful in the reinforcement and sealing of tears as well as the prevention or reduction of scar formation after surgery in addition to other post-surgical complications. Additionally, due to the enhanced adhesive properties of the tissue graft, the grafts are ready for application to the surgical site without the need for sutures.

In one aspect, the grafts described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the grafts described herein can function as a tissue regeneration template that delivers essential wound healing factors, extra-cellular matrix proteins and inflammatory mediators to help reduce inflammation, enhance healing, and reduces scar tissue formation. In this aspect, the micronized placental compositions described herein are used in treating wounds amenable to negative pressure technology, including burns and ulcers, such as chronic ulcers, diabetic ulcers, decubitus ulcers and the like.

In another aspect, the micronized placental tissue is used in conjunction with conventional treatments, including, but not limited to, negative pressure therapy, and may also be used in combination with matrices or scaffolds comprised of biocompatible materials, such as collagen, hyaluronic acid, gelatin or combinations thereof.

In another aspect, the tissue grafts described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the tissue grafts described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the tissue grafts described herein can be used as a protective barrier, where the graft protects the spinal dura from post-surgical trauma from the surrounding surgical site. For example, the grafts can prevent damage to the spinal dura caused by sharp edges from newly cut bone such as vertebrae. In other aspects, the tissue grafts can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the tissue graft can be applied directly to the spinal dura, the surrounding region of the spine to include nerve roots, or a combination thereof. Due to the unique structure of vertebrae, the tissue graft can be cut into any shape or dimension so that it can be placed and affixed at the appropriate position in the subject. For example, when the tissue graft is used for bi-lateral coverage, membranes in the shape of a rectangle allow the tissue graft to fit around the posterior spinal process, which minimizes lateral movement. In addition to minimizing lateral movement, the tissue graft can also provide proximal and distal barrier coverage where the spinal lamina has been removed for exposure to the affected area. In one aspect, to ensure proper placement, the graft can be embossed on the exposed basement membrane of the graft to ensure proper placement of the graft in the subject. In particular, proper graft placement will ensure that the basement membrane of the graft is in direct contact with the spinal dura or surrounding region. For example, proper membrane placement and orientation is important when applying the material in spinal applications where a posterior or anterior approach is utilized.

The grafts are useful in preventing or reducing scar formation that can result from a variety of surgical procedures associated with the spine. The grafts can be used after any procedure in the neck, mid-back, or lower back. Depending upon the application, the epithelium of the amnion membrane can be substantially removed. For example, in posterior procedures such as a laminectomy or discectomy, the epithelium layer is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures. Thus, the grafts described herein provide an unmet need in these procedures.

In other aspects, the epithelial cell layer is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the grafts provide additional protection to the vertebral surgical site by maintaining separation from the peritoneum, larger vessels, and abdominal musculature. The membrane serves as a reduced friction anatomical barrier against adhesions and scaring. For example, the grafts can prevent scar tissue binding major blood vessels to the spine. This is a common problem with post-spinal surgery, which requires a second surgical procedure to address this.

In another aspect, the tissue grafts are useful in dental applications. For example, the grafts can be used around dental implants or in the treatment of advanced gingival recession defect. In another aspect, the grafts can be used in guided tissue regeneration.

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists.

The main types of injuries include tendon and ligament sprains and ruptures in the various joints, with the most common being ACL in the knee and rotator cuff in the shoulder. Non-tendon and ligament procedures include repair of torn knee meniscus and repair of knee cartilage which if left un-treated can lead to osteoarthritis of the joint. Non-surgical options also include injections of anti-inflammatory drugs to inflamed tendons (such as "tennis elbow"), injection of lubricants into joints (such as hyaluronic acid into the knee), as well as physiotherapy and bracing.

In one aspect, the tissue grafts described herein can be used to wrap tendon repairs to prevent scar formation on the healing tendon. They can also provide a protective, enclosed environment for the repair to progress successfully. The tissue grafts can be used as an off-the-shelf tendon and ligament to replace the need to purchase an allograft or perform tendon or ligament transfer.

In other aspects, the tissue grafts described herein can be used in the reinforcement of rotator cuffs. Some rotator cuff tears are large enough that they require a reinforcement matrix to support the repair due to lack of viable native tissue. The tissue grafts described herein can be used as a matrix to reinforce a repair. In one aspect, the tissue grafts described herein can be used to repair knee cartilage. For example, the tissue grafts can be used as a barrier to hold cell cultured chondrocytes or other pro-cartilage regeneration matrix inside a chondral defect. In this aspect, the tissue graft would be utilized as a flap to close the defect and hold the matrix in place.

In one aspect, the tissue grafts can be used to repair peripheral nerves. The tissue graft can be used as a wrap on nerve repairs to prevent scar formation onto the healing nerve. The tissue graft can also provide a protective enclosed environment for the repair to progress successfully. In other aspects, the tissue grafts can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue graft can be used to wrap nerve bundles after prostatectomy procedures. These nerves are responsible for erectile function and possible continence. The tissue grafts can be laid on the nerves to keep them from scarring and possibly damaging the nerves.

In other aspects, the tissue grafts described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In another aspect, the tissue grafts can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The tissue grafts can be used as a patch to reduce the amount of scar tissue in the reproductive system after a surgical procedure. Scar tissue is another form of fibrous tissue and may also contribute to fertility problems. The ability to minimize the amount of scar on the ovaries, or within the fallopian tubes may help with post-operative fertility and even pain. In another aspect, the tissue grafts can be used to reline the uterine wall after severe endometriosis treatments and increase the patient's ability to conceive. In a further aspect, the tissue graft can be used as an anti-adhesion barrier after removal of ovarian cyst or aid in the repair of vaginal wall erosion.

Figure 7:
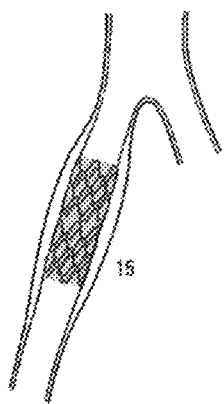
FIG. 7 shows the application of a reinforced tissue graft as arterial stent (15).

In other aspects, the tissue grafts can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts described herein can be used as a patch to support the repair of vascular and cardiac defects caused by operations and complications such as carotid artery repair, coronary artery bypass grafting, congenital heart disease, heart valve repair, and vascular repair (i.e. peripheral vessels). In other aspects, the reinforced tissue graft can be configured into a stent (FIG. 7).

The tissue grafts described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts can be used to facilitate closure of anastomosis, an anti-adhesion barrier for anastomosis, or an anti-adhesion barrier for hernia repair.

In other aspects, the tissue grafts can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts described herein can be used to prevent the additional trauma associated with harvesting the patients' own tissue and save time in surgery. In other aspects, the tissue grafts can be used as a wound covering after adenoidectomy, a wound cover after tonsillectomy, or facilitate repair of the Sniderian membrane.

In other aspects, the tissue grafts described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts described herein can be used as a patch to aid in the healing and prevention of scars; and keloid or cancer revision/removal where careful approximation of soft-tissue edges is not achievable and scar tissue can result. Additionally, the anti-inflammatory properties of the tissue graft can enhance healing as well.

In other aspects, the tissue grafts can be used in ophthalmological applications (e.g., on-lay grafts ocular surface repair) or urological applications (e.g., facilitate closure of the vas deferens during vasectomy reversal or facilitate closure of the vas deferens resulting from trauma).

In one aspect, the tissue grafts can be used in cranial dura repair and replacement, in the elimination of a frenum pull, the regeneration of lost patella tissue, the repair of the Schneiderian membrane in the sinus cavity, soft tissue around dental implants, vestibuloplasty, and guided tissue regeneration.

Figure 5:
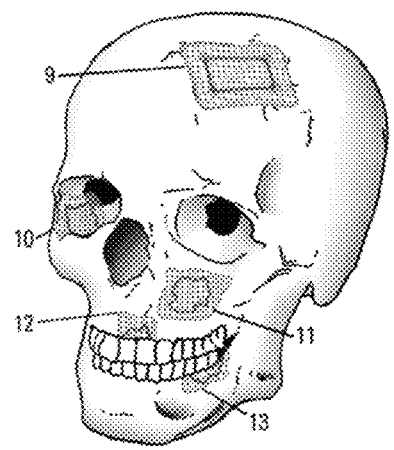
FIG. 5 shows the application of a reinforced tissue graft over a trephine defect (9), orbital defect (10), repair of a sinus (11), maxillary vertical and horizontal bone augmentation (12), and mandibular vertical and horizontal bone augmentation (13).
Figure 6:
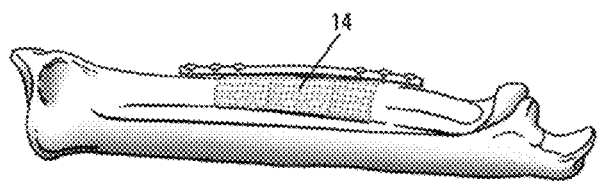
FIG. 6 shows the application of a reinforced tissue graft in a segmental long bone defect (14).

In another aspect, the reinforced tissue grafts can be used in the treatment of bone defects and bone repair. In one aspect, the reinforced tissue grafts can be used in dental surgery to provide primary stability in mandibular and maxillary horizontal and or vertical guided bone regeneration, repair of dental implants, repair of the sinus, and over mandibular block graft donor sites. In other aspects, the reinforced tissue grafts can be used in craniofacial surgery, including but not limited to treatment of bony defects caused from trauma, surgically created bone defects such as burrholes and trephine defects, zygomatic defects, and orbital defects (FIG. 5). In orthopedic surgery, the reinforced tissue grafts can be used to treat bone defects including but not limited to open and closed fractures, segmental defects, osteochondral defects, spinal fusion, and other non-load hearing regeneration procedures. In other aspects, the reinforced tissue grafts can be used in the treatment of a segmental long bone defect (FIG. 6).

Depending upon the application of the graft, the graft can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, one or more membrane layers of the tissue graft absorb the bioactive agent. Upon application of the wet tissue graft with bioactive agent to the wound, the bioactive agent is delivered to the wound over time.

Although the tissue grafts described herein can be applied directly to the tissue of a subject, they can also be applied to a wound dressing that can subsequently be applied to the subject. For example, the wound dressing can be gauze, a bandage or wrap, or any other suitable article capable of containing or affixing the tissue graft that can be applied directly to a subject.

Preparation of Micronized Composition

Example 1

The micronized human amniotic membrane injectable was composed of human amnion as described above and intermediate layer tissue obtained from placenta tissue originated in a hospital, where it is collected during a Cesarean section birth. The micronization of the tissue was performed using a Retsch Oscillating Mill MM400. Phosphate buffer was used as a carrier. The ratio of the injectable was 50 mg/mL. The concentration ratio was 60% (21 mg) amnion and 40% (14 mg) intermediate tissue layer with 0.70 mL of phosphate buffer. The micronized composition can be administered as a dermal filler with a 27 gauge needle in the deep dermis region. A suitable dose would be 0.5 cc to 1.0 cc of the composition described above.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of suitable cross-linking agents and procedures is provided in concurrently filed U.S. Patent Application Ser. No. 61/683,697 entitled PLACENTAL TISSUE GRAFTS MODIFIED WITH A CROSS-LINKING AGENT AND METHODS OF MAKING AND USING THE SAME which application is incorporated herein by reference in its entirety.

A detailed description of micronized placental tissue is provided in concurrently filed U.S. Patent Application Ser. No. 61/683,698 entitled TISSUE GRAFTS COMPOSED OF MICRONIZED PLACENTAL TISSUE AND METHODS OF MAKING AND USING THE SAME which application is incorporated herein by reference in its entirety.

A detailed description of making and using micronized placental tissue and extracts thereof is provided in concurrently filed U.S. Patent Application Ser. No. 61/683,700 entitled MICRONIZED PLACENTAL TISSUE COMPOSITIONS AND METHODS OF MAKING AND USING THE SAME which application is incorporated herein by reference in its entirety.

What is claimed is:

1. A reinforced tissue graft comprising:
a first membrane comprising a placental tissue having a first side and a second side;
a non-resorbable biocompatible mesh having a first side and a second side, wherein the first side of the biocompatible mesh is adjacent to the second side of the first membrane;
a second membrane comprising a placental tissue having a first side and a second side, wherein the first side of the second membrane is adjacent to the second side of the biocompatible mesh; and
optionally including from one up to nine additional membranes on either side of the biocompatible mesh,
wherein at least one of the first membrane, the second membrane, or the additional membranes comprises modified amnion having an intact epithelial cell layer,
wherein each modified amnion in the graft has an intact epithelial cell layer, and
wherein the biocompatible mesh is coated on one or both sides with micronized placental tissue.

2. The tissue graft of claim 1, wherein the first membrane comprises amnion, chorion, or a laminate comprising one or more layers of amnion with one or more layers of chorion.

3. The tissue graft of claim 1, wherein the second membrane comprises amnion, chorion, or a laminate comprising one or more layers of amnion with one or more layers of chorion.

4. The tissue graft of claim 1, wherein the second membrane comprises an amnion/chorion laminate, wherein the chorion is adjacent to the second side of the biocompatible mesh.

5. The tissue graft of claim 4, wherein the amnion comprises an intermediate layer, and wherein the chorion is adjacent to the intermediate layer.

6. The tissue graft of claim 1, wherein the first membrane comprises Wharton's jelly.

7. The tissue graft of claim 1, wherein the first membrane and/or second membrane are crosslinked.

8. The tissue graft of claim 1, wherein the biocompatible mesh has a pore size from 200 microns to 4,000 microns.

9. The tissue graft of claim 1, wherein the biocompatible mesh has a plurality of pores spaced from 1,000 microns to 4,500 microns apart as measured from the center of two pores.

10. The tissue graft of claim 1, wherein the biocompatible mesh has a thickness of 300 microns to 2,000 microns.

11. The tissue graft of claim 1, wherein the biocompatible mesh is made of a thermoplastic resin, polyethylene, ultrahigh weight molecular weight polyethylene, high molecular weight polyolefin, uncoated monofilament polypropylene, polyether ether ketone, polyethylene terephthalate, polytetrafluoroethylene, expanded polytetrafluoroethylene, nylon, or any combination thereof.

12. The tissue graft of claim 1, wherein the micronized placental tissue is applied to the tissue graft by wetting the biocompatible mesh to render it absorbent and contacting the biocompatible mesh with a surface having micronized placental tissue deposited thereon.

13. A wound dressing comprising the tissue graft of claim 1.

* * * * *